(12) United States Patent
Yang et al.

(10) Patent No.: US 12,607,902 B2
(45) Date of Patent: Apr. 21, 2026

(54) APPARATUS AND METHOD FOR AN IMAGING DEVICE

(71) Applicant: Leica Instruments (Singapore) Pte. Ltd., Singapore (SG)

(72) Inventors: Gao Yang, Singapore (SG); Alvin Kok, Singapore (SG)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 546 days.

(21) Appl. No.: 18/167,135

(22) Filed: Feb. 10, 2023

(65) Prior Publication Data

US 2023/0259003 A1 Aug. 17, 2023

(30) Foreign Application Priority Data

Feb. 11, 2022 (DE) ..................... 10 2022 103 281.7

(51) Int. Cl.
| | |
|---|---|
| *G03B 7/00* | (2021.01) |
| *A61B 90/20* | (2016.01) |
| *G02B 7/28* | (2021.01) |
| *G02B 21/00* | (2006.01) |
| *G02B 21/36* | (2006.01) |

(52) U.S. Cl.
CPC ................ *G03B 7/00* (2013.01); *A61B 90/20* (2016.02); *G02B 7/28* (2013.01); *G02B 21/0012* (2013.01); *G02B 21/365* (2013.01)

(58) Field of Classification Search
None
See application file for complete search history.

(56) References Cited

U.S. PATENT DOCUMENTS

| | | | | |
|---|---|---|---|---|
| 8,394,083 | B2 * | 3/2013 | Van Heugten | ........... A61B 3/13 606/5 |
| 8,394,084 | B2 * | 3/2013 | Palankar | ............. A61F 9/00754 606/5 |
| 9,180,051 | B2 * | 11/2015 | Frey | ........................ A61B 90/30 |
| 9,889,043 | B2 * | 2/2018 | Frey | .................... A61F 9/00825 |
| 2017/0189233 | A1 * | 7/2017 | Dewey | ................ A61F 9/00825 |
| 2021/0267434 | A1 | 9/2021 | Yamaguchi et al. | |

FOREIGN PATENT DOCUMENTS

| | | |
|---|---|---|
| DE | 102008041290 A1 | 2/2010 |
| EP | 2833779 B1 | 9/2017 |
| WO | 2020170866 A1 | 8/2020 |
| WO | 2021003304 A1 | 1/2021 |

* cited by examiner

*Primary Examiner* — Robert E. Tallman
(74) *Attorney, Agent, or Firm* — 2SPL Patent Attorneys PartG mbB; Yong Beom Hwang

(57) ABSTRACT

An apparatus is disclosed which is to identify a feature of an image captured from a first focal plane; determining a focus position relative to the first focal plane; and to determine an aperture setting. At the focus position and the aperture setting, a depth of field is provided. The apparatus may be further configured to determine at least one of a second plane and a third plane relative to the first focal plane. At the focus position and the aperture setting, the at least one of the second plane or the third plane is in focus.

20 Claims, 3 Drawing Sheets

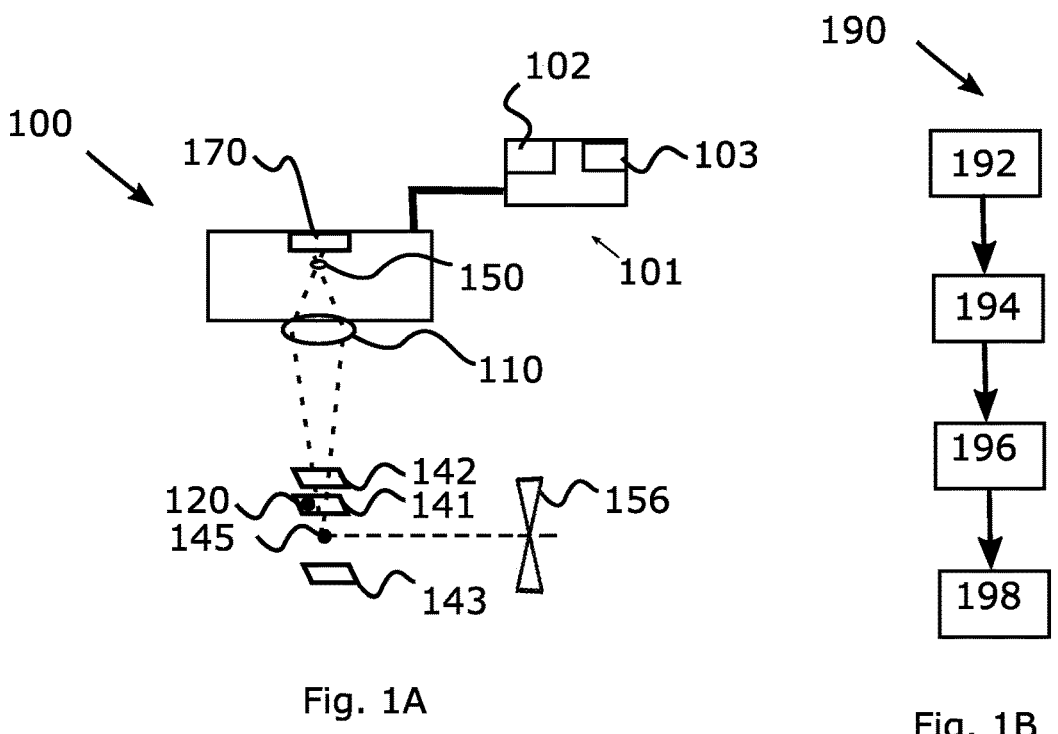
Fig. 1A
Fig. 1B
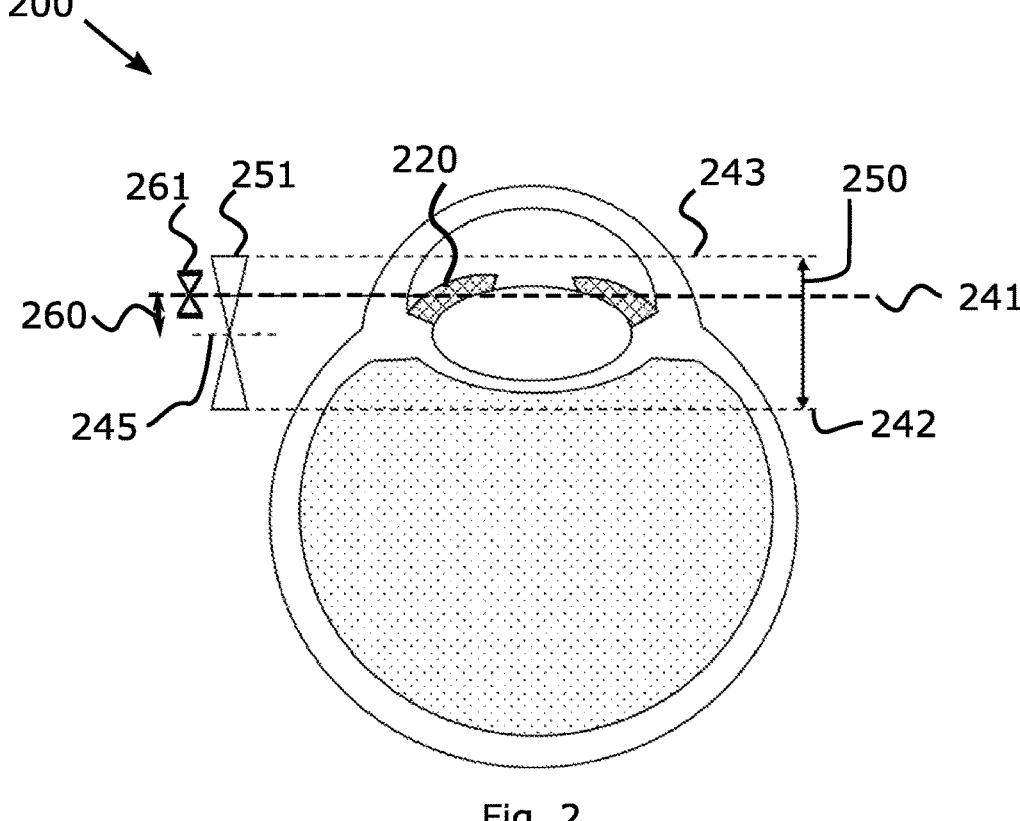
Fig. 2

300

351

343

341, 345

342

322

400

451

422

442

445

443

423

500

501

510

520

APPARATUS AND METHOD FOR AN IMAGING DEVICE

CROSS-REFERENCE TO RELATED APPLICATION

This application claims priority to German Application 10 2022 103 281.7, which was filed on Feb. 11, 2022. The content of this earlier filed application is incorporated by reference herein in its entirety.

TECHNICAL FIELD

Examples relate to an apparatus for determining settings for an imaging device such as for an optical imaging device, e.g. a surgical microscope.

BACKGROUND

The depth of field of an optical imaging device can be influenced by the aperture. Decreasing the aperture can increase the depth of field, which can aid in providing adequate resolution of features which may not be positioned exactly at the focal plane. Particularly in surgical microscopy, a precisely determined focus and aperture setting can aid in resolving features which are of interest to the user.

SUMMARY

An embodiment relates to an apparatus configured for identifying a feature, and in particular an anatomical feature, of an image captured from a first focal plane, determining a focus position relative to the first focal plane, and determining an aperture setting. At the focus position and the aperture setting, a depth of field is provided. In effect, the focus position is determined relative to the focal plane of the anatomical feature. Together with the aperture setting, the focus position being determined relative to the focal plane of the anatomical feature, results in the desired depth of field. For example, the depth of field may include, or be based on, a depth of a surgical site, e.g., such that anatomical features on different focal planes of the depth of field are (also in focus). For example, the identified anatomical feature may be used as point of reference, with the focus position being determined relative to the (first) focal plane in which the anatomical feature lies. For example, the focus position may be determined relative to the first focal plane and the aperture setting may be determined such that a depth of a surgical site is covered by the resulting depth of field. The apparatus can aid in visualizing features at different depths in a field of view.

In some examples, the apparatus is configured for also determining at least one of a second plane or a third plane relative to the first focal plane. At the focus position and the aperture setting, the at least one of the second plane or the third plane may be in focus. In other words, the focus position and aperture may be determined such that at least one of the second plane and the third plane are in focus. For example, the focus position may be determined such that the first place, the second plane (and optionally the third plane) are in focus. The apparatus can aid in visualizing features, and in particular anatomical features, at different depths in a field of view, particularly features at the second and/or third plane.

In some examples, the apparatus is further configured for determining the focus position by determining an offset from the first focal plane to the focus position. A wider range of (anatomical) features can be put into focus by offsetting the focus from the first focal plane. The focus position can be between the second and third planes. The depth of field can be set so that the (anatomical) features at the second and third planes are in focus, such as to aid in the visualization of the field of view.

For example, the aperture setting may be the maximum aperture for which, at the focus position, each of the second and third planes is in focus. A maximum aperture can allow greater light collection and increase signal/noise, and/or allow for reduced irradiation of the sample by allowing lower fluence.

In some examples, the apparatus is further configured for outputting the focus position and the aperture setting for controlling a focus and an aperture of an imaging device. The imaging device can be controlled to provide for visualization of (anatomical) features at multiple planes, e.g. simultaneously.

In various examples, the apparatus is further configured for controlling an autofocus procedure to focus to the first focal plane. The determination of the first focal plane by autofocus can provide for a standard starting point from which to base the determination of different planes of (anatomical) features.

In some examples, the apparatus is further configured for outputting a fully open aperture setting for capturing the image from the first focal plane. A fully open aperture at capture of the first focal plane can more accurately set the z-position of the apparatus, making subsequent determinations of planes more accurate as well, e.g. those planes which are determined relative to the first focal plane.

Herein the anatomical feature can be an iris of an eye of a subject or a corneal limbus of an eye. Such a (anatomical) feature can provide a high contrast and/or known starting plane from which to base subsequent determinations of planes.

In some examples, at least one of:

(1a) the focus position, the second plane, and the third plane are configured for including an anteriormost outer surface of a cornea and posterior lens capsule in focus; or (1b) the focus position, the second plane, and the third plane are configured for including an anteriormost inner surface of a cornea and posterior lens capsule in focus; or (2) the focus position, the second plane, and the third plane are configured for including a retina in a center of a field of view and the retina in a periphery of the field of view in focus; or (3) the focus position, the second plane, and the third plane are configured for including a nearest surface of a cornea and a farthest surface of the cornea in focus (cornea transplant); or (4) the focus position, the second plane, and the third plane are configured for including an anteriormost outer surface of the cornea and the limbus in focus (for endothelial keratoplasties); or (5) the focus position, the second plane, and the third plane are configured for including an anteriormost outer surface of the cornea and a plane 800 micrometers posterior thereto in focus (for endothelial keratoplasties).

The examples above can aid surgeons in providing multiple (anatomical) features in focus which are in different planes. Automation, for example, of the focus position and/or aperture setting, may provide the surgeon with a better resoled image at greater convenience than requiring manual adjustment and/or trial-and-error adjustments.

In some examples, the apparatus is further configured for at least one of: identifying a second (anatomical) feature of the second focal plane, or identifying a third (anatomical) feature of the third plane. Identifying (anatomical) features can aid in ensuring a high-content and informative image for the user. For example, a computer algorithm, such as a feature recognition algorithm and/or machine learning algorithm may identify the first, second and/or third (anatomical) features.

In some examples, the second (anatomical) feature is the cornea and the third feature is the (anatomical) posterior lens capsule. Alternatively, the second (anatomical) feature may be the retina at a center of a field of view and the third feature may be at the periphery of the field of view. Having these particular (anatomical) features in focus can aid a surgeon in visualizing a surgical field.

In some examples, the apparatus is further configured for receiving input. The input may include at least one of: the identification of the (anatomical) feature, a depth of field, a first distance from the first focal plane to the second focal plane, a second distance from the first focal plane to the third plane, or a third distance from the second focal plane to the third plane. The input may be received from a user or from memory. Providing input increases flexibility in how to determine the parameters particularly the aperture and focus.

For example, the apparatus may be further configured for identifying the (anatomical) feature by a feature recognition algorithm. An algorithm can aid in simplifying the determination of the settings, particularly the aperture and focus. The algorithm can alternatively/additionally identify second and/or third (anatomical) features which may be in planes other than the first focal plane.

In various examples, the apparatus may be further configured for identifying the feature by a trained machine learning algorithm. A machine learning algorithm can aid in simplifying the determination of the settings, particularly the aperture and focus.

For example, the apparatus may be further configured for determining at least one of the (anatomical) features, the second plane, or the third plane based on a surgical workflow. The determination of the (anatomical) feature and/or plane(s) based on the workflow can aid in more precise determination of the settings, particularly the aperture and focus. The apparatus may also determine a step of the surgical workflow, e.g. to aid in determining the optical settings (such as focus point and aperture) which aid in visualizing the structures within the field of view which are relevant for the surgical workflow.

For example, the apparatus may further comprise a detector for capturing images including the image from the first focal plane; an adjustable lens assembly for focusing, and an adjustable aperture. These components can aid in providing the optical settings for optimal visualization of the field of view.

In various examples, the apparatus is further configured for receiving input from a second imaging device such as an optical coherence tomographic device. A second imaging device can provide increased accuracy for the determination of (anatomical) feature(s) and/or planes, which can allow for more accurate focusing to include the (anatomical) feature(s) at different planes of interest.

In some examples, the apparatus is further configured for determining the second plane based on a second (anatomical) feature of the second plane. Determining the plane(s)

based on (anatomical) feature(s) can increase accuracy of the settings, e.g. the focus position and aperture.

Herein is disclosed a method of controlling an imaging device, including identifying a (anatomical) feature of an image captured from a first focal plane; determining a focus position; determining an aperture setting; and outputting the focus position and the aperture setting for controlling a focus and an aperture of an imaging device. The method can aid in visualizing (anatomical) features at different depths in a field of view.

Herein is disclosed a method of controlling an imaging device, further comprising determining at least one of a second plane or a third plane relative to the first focal plane; wherein at the focus position and the aperture setting, the at least one of the second or third planes is in focus. The method can aid in visualizing (anatomical) features at different depths in a field of view. Herein is disclosed a computer program having a program code for performing the method of controlling the imaging device.

BRIEF DESCRIPTION OF THE FIGURES

Some examples of apparatuses and/or methods will be described in the following by way of example only, and with reference to the accompanying figures.

FIG. 1A illustrates an imaging device.

FIG. 1B illustrates a method of controlling an imaging device.

FIG. 2 illustrates an eye.

DETAILED DESCRIPTION

Figure 3:
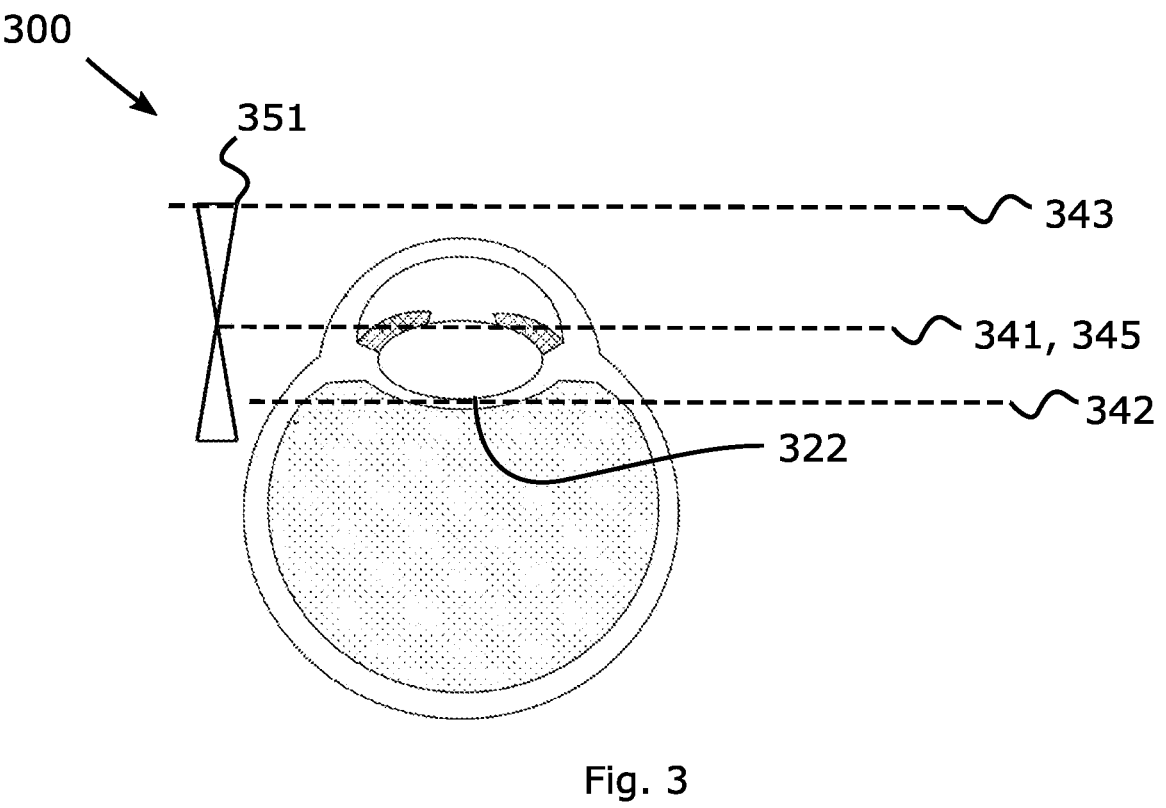
FIG. 3 illustrates an eye.
Figure 3:

Various examples will now be described more fully with reference to the accompanying drawings in which some examples are illustrated. In the figures, the thicknesses of lines, layers and/or regions may be exaggerated for clarity.

FIG. 1A illustrates according to an example an imaging device 100 for capturing an image, e.g. an image which is collected when the imaging device 100 is focused on a focus position 145. The imaging device 100 can have an aperture 150 which is adjustable. Light collected by the imaging device 100 can pass through a lens assembly 110 and the aperture 150, and can be captured by a detector 170. The focus position 145 and aperture setting can be determined, e.g. such that a depth of field 156 is provided. The depth of field 156 can extend axially toward and away from the focus position 145, e.g. toward and away from the imaging device 100 in a z-direction.

The detector 170 can be for capturing images including the image from the first focal plane, as well as subsequently captured images, e.g. images captured after the focus position and/or aperture setting is determined. The adjustable lens assembly 110 can be for focusing.

The imaging device 100 can be communicatively coupled to an apparatus 101 such as an apparatus 101 that includes at least one processor 102 and at least one memory 103. The apparatus 101 can be for controlling the imaging device 100, e.g. including for the output of control signals to control the focus and/or aperture setting, e.g. the lens assembly 110 and/or aperture 150. Apparatus 101 can receive captured images from the imaging device 100. The imaging device 100 can be an ophthalmic microscope, for example. Other surgical microscopes are possible.

FIG. 1A also shows an (anatomical) feature 120 of/at a first focal plane 141. A second and third plane 142, 143 are also shown. In the example of FIG. 1A, when the imaging device 100 is at the focus position 145 and a determinable aperture setting, the depth of field 156 is provided, e.g. a depth of field 156 that includes at least one of the second plane 142 or the third plane 143. The focus position 145 that is determined can be between the second and third planes 142, 143. The aperture setting can be determined to be the maximum aperture for which, at the focus position 145, each of the second and third planes is in focus.

Features of interest may be identified in the second and/or third planes 142, 143. Alternatively/additionally, the second and/or third planes 142, 143 can be determined from data in memory. For example, there can be a known spatial relationship (e.g. a distance, particularly along the optical axis of the imaging device 100, and/or relative position) between the feature 120 and a second and/or third feature which are, respectively, known to be or expected to be in the second and/or third planes 142, 143.

For example, the first focal plane 141 is determined by autofocus, which may include an algorithm for maximizing contrast and/or maximizing contrast in combination with identifying the feature 120 of the focal plane 141. The anatomical feature 120 can be identified during and/or immediately after an autofocus procedure.

FIG. 1B illustrates a method 190 of controlling an imaging device, such as the imaging device 100 of FIG. 1A including in its various optional forms and configurations described herein. The method includes identifying 192 a feature 120 of (i.e., in) an image captured from a first focal plane 141, determining 194 a focus position 145 (which may be coplanar with the first focal plane 141 or offset from the first focal plane 141), determining 196 an aperture setting. The method can also include outputting 198 the focus position and the aperture setting for controlling a focus and an aperture of an imaging device. Herein the focus position can mean the position(s)/setting(s) of optical element(s) such as at least one lens, e.g. of the lens assembly 110. The positions and/or settings can have the effect of changing the focus position, e.g. the point/plane at which, in the object space, the imaging device 100 is focused. Before identifying 192 the (anatomical) feature 120, the method can include controlling an autofocus and/or focus setting procedure which may result in the focusing to the first focal plane. Alternatively/additionally, an autofocus procedure can include identifying 192 the feature 120 and/or maximizing contrast of the feature 120.

For example, the method 190 can include outputting an open aperture setting (e.g. a fully open setting) for capturing the image in which the feature 120 is identified 192. The autofocus procedure, which can precede the steps shown in FIG. 1B, can use an open aperture setting (e.g. fully open). An open aperture can reduce the depth of field and thus more precisely determine the first focal plane 141. The subsequent determination of the focal position 145 and/or aperture setting can be more precise as a result of the greater precision of the first focal plane 141 determination. The method can be modified according to examples described herein, including those examples described in relation to the imaging device 100 and/or apparatus 101 described herein.

Herein is disclosed a computer program having a program code for performing any one or more of the methods described herein, such as for control of an imaging device 100.

FIG. 2 illustrates an example of an object in object space, in this case an eye 200, shown in cross-section. Other objects are contemplated, such as surgical scenes which include features of interest in different types of surgery.

The example of FIG. 2 aids in understanding the functions of an apparatus 101 for determining a focus position 145 and aperture setting, according to embodiments described herein. In the example of FIG. 2, an imaging device 100 captures an image from a first focal plane 241. A (anatomical) feature 220 (e.g. an iris or corneal limbus, or the macula such as for retinal surgery) is identified of (in) the image. An autofocus procedure may determine the first focal plane 241 such as by maximizing contrast. Alternatively/additionally, a computer algorithm such as a machine learning algorithm can identify the feature 220.

The identification of the (anatomical) feature 220 may be correlated with the presence of another (anatomical) feature(s), e.g. other expected feature(s)s which may be identified or expected, e.g. in the field of view. The other feature(s) may be at the same 241 or different focal plane as the feature 220.

FIG. 2 illustrates a relatively small depth of field 261 (e.g. a depth of field that extends a relatively short distance along the optical axis) at the first focal plane for a relatively large aperture with a relatively small depth of field 261 (e.g. in comparison to the depth of field 261). After the focus position 245 and aperture setting is determined, the depth of field 250 is provided. The focus position 245 and aperture setting can be determined such that at least one of a second plane 242 and a third plane 243 is in focus, e.g. when the imaging device 100 is at the focus position 245 and depth of field 250 of the determined aperture setting. For example, the second plane 242 can coincide with the expected or identified plane of a second (anatomical) feature such as the posterior surface of the lens capsule.

The second and/or third plane 242, 243 may be outside the maximum depth of field of the imaging device when focused at the first focal plane. When focused at a particularly large offset from the first focal plane 241, for example, the second and/or third plane 242 which is in focus at the determined focus position 245, may be outside the maximum depth of field of the device when focused at the first focal plane 241. It can be advantageous to provide for an offset which allows for the second and/or third plane 242, 243 to be in focus, and/or may overcome hardware limitations on the depth of field if the focal position is not offset.

In an embodiment, determining the focus position 245 can include determining an offset 260 from the first focal plane 241 to the focus position 245, e.g. a nonzero focus offset. In an alternative, there is no offset or the offset is determined to be zero. A nonzero focus offset can be determined when the second plane 242 is outside the maximum depth of field of the instrument when the imaging device 100 is focused at the first focal plane 241. For example, there may be a minimum aperture diameter which may determine the maximum depth of field. When a (anatomical) feature of a second plane 242 is beyond the depth of field when the imaging device 100 is focused to the first focal plane 241, a nonzero focus offset can be determined, e.g. such that, at the focus position 245, the second plane 242 is in focus. At least one of the first focal plane 241, the second plane 242, and a third plane 243 can be in focus at the determined focus position 245 and aperture setting. A third (anatomical) feature can be present (e.g. expected and/or identified) in the third plane 243.

In the example of FIG. 2, the maximum depth of field 251 is depicted being centered at the focus position 245 rather than centered at the first focal plane 241. The example of FIG. 2 illustrates a case when the offset 260 from the first focal plane 241 to the focus position 245 is nonzero. A zero offset 260 can be determined when, for example, the second plane 242 is within the maximum depth of field 251 when the imaging device 200 is focused at the first focal plane 241. The depth of field at any given focal position is variable and depends on the aperture setting.

For example, the apparatus 101 determines that the second plane 242 is outside the possible depth of field of the imaging device 100 when focused at the first focal plane 141. The second plane 242 may be determined from memory (e.g. from a database that provides data of the relative positions of (anatomical) features of interest). For example, the relative depths of features of interest can be used to determine the relative positions of planes, e.g. the position(s) of the second plane 242 and/or third plane 242 relative to the first focal plane 241.

Alternatively/additionally, the second plane 242 may be determined by the apparatus 101 from images, such as live images from the imaging device 100 and/or a second imaging device. For example, the imaging device 100 can capture images at more than one focus position and/or aperture setting and identify a second (anatomical) feature. Alternatively/additionally, the second plane may be determined from a second imaging device which provides depth information. For example, optical coherence tomography, OCT, may provide images which allow for the identification of different planes and/or (anatomical) features in the field of view. For example, the interfaces of the cornea, lens capsule, and/or retina can be determined from OCT images. The second and/or third plane may be determined based on OCT images and/or features (such as anatomical features, particularly of the eye) identified from images such as OCT images.

It can be desirable to be able to have optical settings of the imaging device 100, e.g. determined by the apparatus 101, that allow features such as anatomical features in different planes to simultaneously be in focus. FIG. 2 shows second plane 242 and a third plane 243 which may be planes where respective anatomical features are determined and/or expected. It is possible to determine a focus position 245 (relative to the first focal plane 241) and aperture setting which is such that the second plane 242 and the third plane 243 are in focus.

In another case, after capture of the image at the first focal plane 241, the second plane 242 is determined to be within the maximum depth of field when the focus position 245 is at the first focal plane 241. In such a case, the offset 260 can be zero. The focus position 245 that is determined can be the same as the first focal plane 241. The aperture setting can be determined such that the depth of field extends at least to the second plane 242. It is possible that the image captured from the first focal plane 241 can be captured at a wide aperture, such as at maximum aperture, and the aperture stopped down subsequently such that the second and/or third planes 242, 243 are in focus. Using a wide aperture particularly during autofocus procedures, e.g. before capturing the image from the first focal plane 241 in which the feature 220 is identified, can more precisely determine the focus position of the imaging device 100.

FIG. 3 illustrates an example of a sample, an eye 300, in the object space of an imaging device 100. In FIG. 3, there is illustrated an example in which the maximum depth of field 351 is such that at zero offset (zero focus offset) from the first focal plane 341, the second plane 342 can be in focus. For example, a second (anatomical) feature 322 can be in the second plane (for example the posterior surface of the lens). The determined focal position 345 can be in the same plane as the first focal plane 341. At the determined focal position 345, the second plane 342, which, as shown in FIG. 3, can be offset from the first focal plane 341, is in focus when the device 100 is at the determined focal position 345 and determined aperture setting. The focus offset, which may be zero, may be determined based on the determination of the second plane 342 and/or the third plane 343.

The determination of the second plane 342 and/or third plane 343 can be based on a relative position of a feature, e.g. the position of a second feature 322 which is in the second plane 342 and/or the position of a third feature in the third plane 343.

A third plane 343 can be determined which can correspond to a plane located in the opposite direction from the focal position 345 as the second plane 342; the third plane 343 can be at the same distance from the determined focus position 345 as the second plane 342.

In an example, by determining the second plane 342, the third plane is automatically determined as being the plane at the same distance from the focus position 345 as the second plane 342 in the opposite direction from the focus position 345. After the third plane 343 is determined in such a manner, the algorithm, computer program, and/or apparatus 101 can determine which features are expected to be in focus. The focus position can be adjusted further, for example, to include another (anatomical) feature (e.g. a third feature) in focus, e.g. within the depth of field at the aperture setting, e.g. while keeping the second feature 322 of the second plane 342 within the depth of field.

A focus offset may be determined to be nonzero.

In the example of FIG. 2, the second plane 242 and the third plane 243 are at different distances from the first focal plane 241; alternatively/additionally the offset 260 is determined so that the second plane 242 and the third plane 243, are equidistance from the focal position 245.

There can be a second feature 322 of interest located in the second plane 342. In the example of FIG. 3, the second feature 322 lies within the maximum depth of field of the imaging device when at the focal position 345. The aperture setting can be determined such that the second plane 342 is in focus when at the focus position 345.

Figure 4:
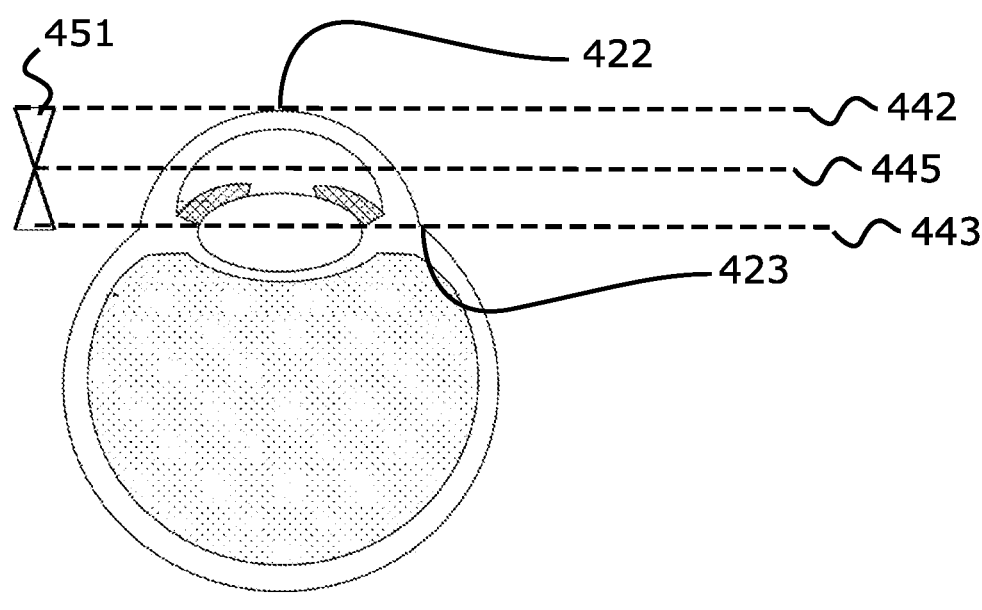
FIG. 4 illustrates an eye.

FIG. 4 illustrates another example of cross section of an eye 400 in the object space of an imaging device, such as the imaging device 100 of FIG. 1, e.g. being controlled by the apparatus 101. In FIG. 4, a second plane 442 includes a second feature 422 which can be the anteriormost outer surface of a cornea. The focal position 445 is between the second plane 442 and the third plane 443. The third plane 443 includes a third feature 423 which can be the limbus. The focal position 445 and aperture setting can be determined so that the second and third planes 442, 443 are each in focus, e.g. after the (first) feature (see FIG. 1 feature 120 for example) is identified of an image captured from a first focal plane (see FIG. 1 plane 141 for example). The first focal plane can be the plane of focus of an autofocus procedure, such as one that maximizes contrast. Alternatively/additionally, the autofocus procedure may include capturing an image at a wide aperture setting (e.g. a maximum aperture) which may increase the precision/accuracy of the focus position.

The second 422 and/or third feature 423 can be expected (anatomical) feature(s). For example, the second feature 422 may be expected to be in the second plane 442. A third feature 423 can be expected to be in the third plane 443. Expected features may be features which are determined based on data stored in memory, such as images. Expected features may be determined based on computer algorithms such as feature recognition, e.g. using a machine learning algorithm. Alternatively/additionally, expected features within the field of view may be determined based on images from a second imaging device (e.g. an OCT).

Alternatively/additionally, the second and/or third planes 442, 443 can be determined based on the relative positions of any one or more of: the feature identified in the first focal plane (see first focal plane 341 for example), a second feature 422 in the second plane 442, or a third feature 423 in a third plane 443. For example, the relative positions of such (anatomical) features can be used to determine the focus position 445, depth of field 451 at the focus position 445, and/or aperture setting such that at least one of the second and/or third planes 442, 443 is in focus. A focus position 445 and aperture setting can be determined so that each of the second and third planes 442, 443 are in focus.

Regarding possible configurations of the focus position, second plane, and third plane, some alternative/additional examples are provided:

(1a) the focus position, the second plane, and the third plane are configured for including an anteriormost outer surface of a cornea and posterior lens capsule in focus;

(1b) the focus position, the second plane, and the third plane are configured for including an anteriormost inner surface of a cornea and posterior lens capsule in focus;

(2) the focus position, the second plane, and the third plane are configured for including a retina in a center of a field of view and the retina in a periphery of the field of view in focus;

(3) the focus position, the second plane, and the third plane are configured for including a nearest surface of a cornea and a farthest surface of the cornea in focus (e.g. during a cornea transplant procedure);

(4) the focus position, the second plane, and the third plane are configured for including an anteriormost outer surface of the cornea and the limbus in focus (e.g. for endothelial keratoplasties);

(5) the focus position, the second plane, and the third plane are configured for including an anteriormost outer surface of the cornea and a plane 800 micrometers posterior thereto in focus (e.g. for endothelial keratoplasties).

In the examples herein, such as those listed above, the aperture setting can be determined such that each of the second or third planes are in focus when the imaging device 100 is at the determined focus position 145 and aperture setting. Alternatively, at least one of the second or third planes are in focus when the imaging device 100 is at the determined focus position 145 and aperture setting. In the examples above, the anatomical features described can be examples of the first, second, and/or third features as described herein. For example, the anatomical features of each example above are examples of the second and third features which are each in focus at the determined focal position and aperture setting, e.g. after identifying a first feature (which may be the limbus or iris), and determining the focal position and aperture.

It is possible that the apparatus 101 (e.g. an apparatus 101 that controls the imaging device 100) is configured to identify, in addition to the feature of the first focal plane, additional (anatomical) features. For example, the apparatus 101 can identify at least one of a second feature of the second plane or a third feature of a third plane. Alternatively/additionally, the apparatus 101 can receive data to determine at least one of the second plane and third plane, e.g. data that provides the relative positions of the first focal plane and at least one of the second plane and third plane. Confirmation of the identification of the second and/or third feature can be from an image captured from the determined focus position (e.g. by a feature recognition algorithm). Such confirmation may show that the determined focus position and aperture setting is adequately providing the depth of field for the user.

In an example, the second (anatomical) feature is the cornea and the third feature is the posterior lens capsule. In another example, the second (anatomical) feature is the retina at a center of a field of view and the third feature is at the periphery of the field of view.

It is possible that the apparatus 101 can receive input (e.g. from a user and/or from memory). The received input can include at least one of the identification of the feature, a depth of field (e.g. a depth of field of an aperture setting), a first distance from the first focal plane to the second focal plane, a second distance from the first focal plane to the third plane, or a third distance from the second focal plane to the third plane.

Identifying at least one of the feature (of the image captured from the first focal plane), the second feature, or the third feature can be by a feature recognition algorithm and/or trained machine learning algorithm. Determining the (anatomical) feature(s), the second plane, or the third plane can be based on a surgical workflow. For example, the surgical workflow may determine which anatomical features are of interest, e.g. which feature(s) should be in focus. It is possible that image recognition algorithms may be used to identify a stage of a surgical workflow, and the determined surgical workflow stage is subsequently used to determine the focus position and/or aperture, e.g. by determining the second and/or third planes.

Herein, the apparatus 101 can be communicatively coupled to a second imaging device (such as an optical coherence tomographic imaging device). For example, the apparatus 101 can receive input from the second imaging device for determination of any one or more of the first focal plane, second plane, third plane, second feature, or third feature.

Herein a (anatomical) feature can be determined based on the capture of one or more images by the imaging device(s). The feature(s) can be identified in any one or more of the captured images. A feature can alternatively/additionally be determined based on data stored in memory. For example, the relative positions of various anatomical features can be stored in memory. When a feature is identified in the image captured from a focal plane, the relative positions of other feature(s) can be determined based on their relative distances and orientations. A feature can be an anatomical feature of a patient. The relative distances and/or orientations of multiple features can be determined by capturing multiple images and identifying the features and/or by accessing data in memory from which the relative distances and/or orientations can be derived.

Herein, an imaging device such as imaging device 100 can be a surgical microscope such as an ophthalmic microscope. The detector 170 can be a camera, for example a digital camera. An ophthalmic microscope can be used in cornea, cataract, and retina surgeries, for example. The microscope can be focused at a distance which may be optimized (e.g. using working distance of 175 mm, 200 mm, or 225 mm). Various procedures may be optimal at various ranges of depths to be clearly visible. Herein are described an apparatus, imaging device, and method of operation thereof for controlling various working parameters such as the focus and aperture setting of an imaging device to aid the user of the device in visualization to perform sensitive and/or precise tasks, such as a surgery.

In cataract surgeries, for example, the surgeon may benefit by seeing from just below the top of cornea to the back of the posterior capsule. In retinal surgeries, the surgeon may benefit by seeing a sharply focused image at the periphery and the retina, which may allow the user to avoid refocusing which can be inconvenient and distracting.

Conventional contrast-based autofocus can provide an image and/or determine a plane of focus that depends on what features contain the highest contrast. Alternatively/ additionally, user input may partially determine the plane of focus. Autofocus procedures may not include algorithms for sophisticated determination of the depth of field (DoF) and/or aperture setting, e.g. around the feature. Stereopsis can be similarly limited in the determination of depth of field and/or what features are in focus.

Herein is disclosed how to include recognition of one or more features to determine a depth of field, focus position, and/or aperture setting, which can allow high resolution (e.g. focused) visualization of one or more features of a sample, particularly when feature are located at different axial distances along the optical axis of the imaging device. For example, herein multiple features of eye anatomy can be visualized when the configurations and/or methods described herein are used. Such configurations and/or methods can be combined, including combinations with autofocusing and determination/recognition of the surgical workflow.

The imaging devices described herein can allow determining a focus position, aperture setting, and/or depth of field, e.g. for a surgical scene, e.g. for a patient undergoing a procedure. Conventional contrast-based autofocus may depend on what features have high contrast, or user input. Conventional contrast-based autofocus may not account for the placement of depth of field (DoF) around the feature in focus. Stereopsis presents similar limitations.

The imaging devices described herein may have one or more digital video cameras, video signal processors, an electronically adjustable focus (e.g. by using a lens assembly), and/or electronically adjustable apertures/diaphragms (e.g. by the use of actuators) in the optical path for the detector which is configured for capturing images.

In example, the depth of a surgical site (e.g. anterior chamber depth of the eye) can be determined preoperatively, e.g. to determine the relative positions of features of interest (e.g. the feature of the first focal plane, the second feature, and/or the third feature, as described herein). It is possible that data for determining such positions can be stored in memory (e.g. input into the apparatus 101 and/or imaging device 100). Alternatively/additionally, it is possible to determine depth and/or the relative positions of features by recognition of the features in captured image(s) from the imaging device 100, alone or in combination with data from memory or data from a second imaging device.

At least one processor can be used for the methods and apparatuses described herein. processor(s) can calculate a required depth of field, for example. For example, knowing the imaging device's depth of field relation with aperture, working distance, and/or zoom settings, the processor(s)s can determine/select an aperture setting to provide a desired/ required DoF. By outputting a control signal (e.g. from an apparatus 101), the aperture setting can be applied at the imaging device 100. Actuators can be controlled to realize settings such as the settings of the aperture 150 and/or lens assembly 110. Alternatively/additionally, illumination can be adjusted to compensate for the change in light transmission due to aperture/diaphragm adjustments to maintain brightness and video signal-to-noise ratio. Smaller aperture settings may be coupled with increases of illumination, and larger aperture settings may allow for decreased illumination.

The processor(s)s of the apparatus 101 can analyze the image(s). The processor(s) can detect and localize a surgical site of interest for the microscope to be optimally focused on (e.g. iris or limbus of the eye). Alternatively/additionally, the processor(s) may identify (anatomical) feature(s). To achieve automatic identification, detection, and/or localization, a machine-learning system can be trained using labelled images of the tissue features taken under the microscope. Alternative/additional algorithms are described hereinbelow. Features of training images can be labeled in the data used for training the algorithm, e.g. to train the algorithm for feature recognition.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output. By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g. sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g. a classification algorithm, a regression algorithm or a similarity learning algorithm. Classification algorithms may be used when the outputs are restricted to a limited set of values (categorical variables), i.e. the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning, (only) input data might be supplied and an unsupervised learning algorithm may be used to find structure in the input data (e.g. by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment. Based on the taken actions, a reward is calculated. Reinforcement learning is based on training the one or more software agents to choose the actions such that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component. Feature learning algorithms, which may be called representation learning algorithms, may preserve the information in their input but also transform it in a way that makes it useful, often as a pre-processing step before performing classification or predictions. Feature learning may be based on principal components analysis or cluster analysis, for example.

In some examples, anomaly detection (i.e. outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted as a classification tree, if continuous values are used, the decision tree may be denoted as a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge (e.g. based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receive input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g. of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e. support vector networks) are supervised learning models with associated learning algorithms that may be used to analyze data (e.g. in classification or regression analysis). Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

Figure 5:
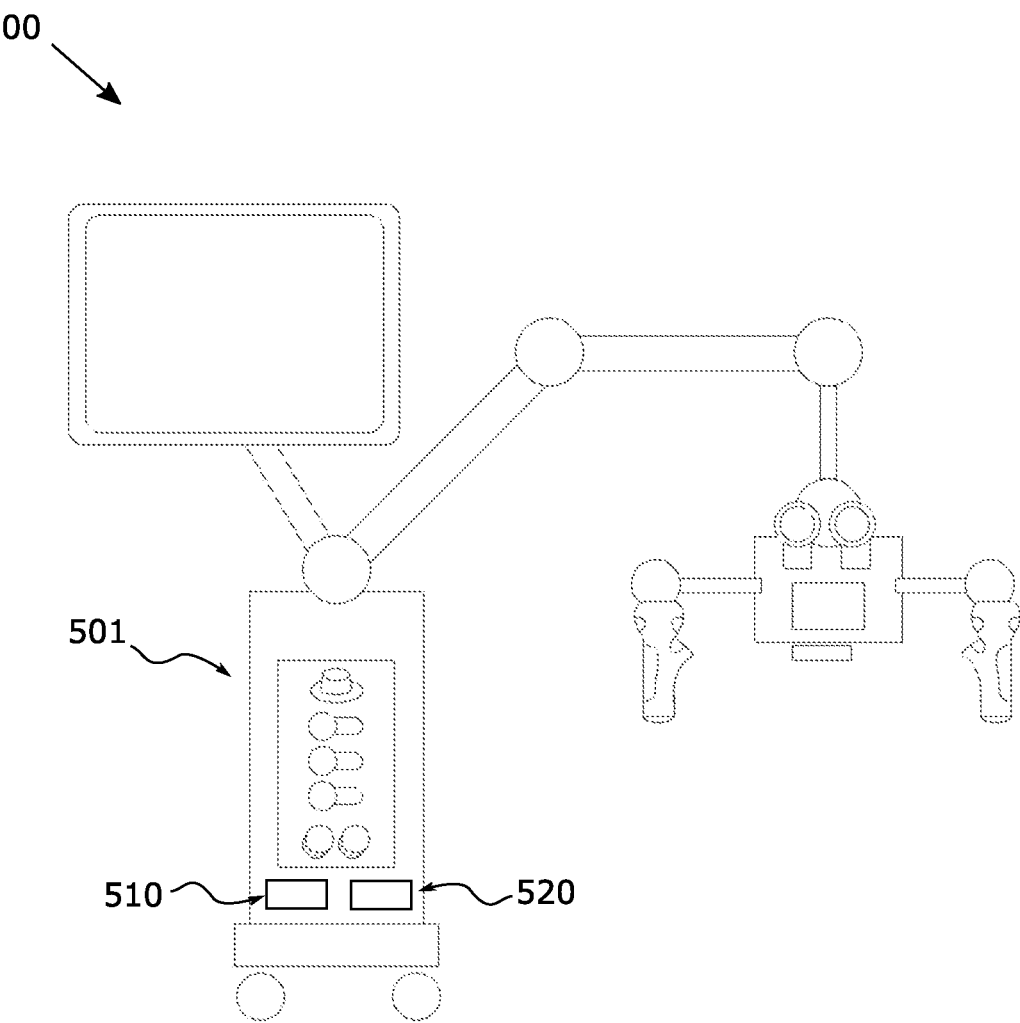
FIG. 5 illustrates a surgical imaging device.

FIG. 5 illustrates a surgical imaging device, such as the imaging device described with respect to FIG. 1. The surgical imaging device 500 of FIG. 5 may include an apparatus 501 for control. Alternatively/additionally, an apparatus 501 for control of the surgical imaging device 500 can be communicatively coupled to the device 500. For example, the surgical imaging device 500 includes a computer device (e.g. personal computer, laptop, tablet computer or mobile phone) with one or more processors 910 and memory 920 (which may include one or more memory devices). The memory 920 can be located in the computer device and/or be in a distributed computing system (e.g. cloud computing system with the one or more processors 910 and one or more memories 920 distributed at various locations, for example, at a local client and one or more remote server farms and/or data centers). The surgical imaging device 900 may include a data processing system that includes a system bus to couple the various components of the surgical imaging device 900. The system bus may provide communication links among the various components of the surgical imaging device 900 and may be implemented as a single bus, as a combination of buses, or in any other suitable manner.

An electronic assembly may be coupled to the system bus. The electronic assembly may include any circuit or combination of circuits. In one embodiment, the electronic assembly includes a processor which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA) of the microscope or a microscope component (e.g. camera) or any other type of processor or processing circuit. Other types of circuits that may be included in electronic assembly may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The surgical imaging device 900 can include one or more memories 920, which in turn may include one or more memory elements suitable to the particular application, such as a main memory in the form of random access memory (RAM), one or more hard drives, and/or one or more drives that handle removable media such as compact disks (CD), flash memory cards, digital video disk (DVD), and the like.

The surgical imaging device 500 may also include a display, one or more speakers, and/or a keyboard and/or controller, which can include a mouse, trackball, touch screen, voice-recognition device, or any other device that permits a system user to input information into and receive information from the surgical imaging device 500.

Additionally, the surgical imaging device 500 may include a microscope connected to a computer device or a distributed computing system. The surgical imaging device 500 can include a detector for acquiring data for images.

Additionally, the surgical imaging device 500 may include a microscope connected to a computer device or a distributed computing system. The microscope may be configured to generate biology-related image-based input training data by taking an image from a biological specimen.

Herein, a microscope may be a light microscope (e.g. diffraction limited or sub-diffraction limit microscope as, for example, a super-resolution microscope or nanoscope). The microscope may be a stand-alone microscope or a microscope system with attached components (e.g. confocal scanners, additional cameras, lasers, climate chambers, automated loading mechanisms, liquid handling systems, optical components attached, like additional multiphoton light paths, lightsheet imaging, optical tweezers and more). Other imaging modalities may be used as well, such as modalities for imaging objects related to tissues, biological specimens, and the like (e.g. proteins, nucleic acids, lipids). For example, a microscope according to an embodiment described above or below may enable deep discovery microscopy.

The imaging device 500 can include a detector, which may be a camera, for acquiring images from a surgical site. The detector can be part of a surgical imaging device such as a microscope shown.

FIG. 5 illustrates an apparatus 501 which can include an image processing device which can couple to a microscope. An image processing device may include the processor 510, e.g. a computer processor. The imaging device (e.g. surgical imaging device 500) can be communicatively coupled to memory and/or include an internally located memory 520. The device 501 can have a display or provide an output for display. The image processing device 501 can be coupled to (or be part of) a surgical imaging device 500. The image processing device Scan be coupled to a microscope, for example. An image processing device 501 and imaging apparatus such as a microscope can form a surgical imaging device 500.

Images for display can include the real-time image of the surgery (e.g. the live image acquired by the detector.

The processor 510 can be used to perform the methods described herein, such as methods of imaging processing, determining settings (e.g. aperture settings and focus positions), features, and/or planes.

For example, during surgery, the apparatus 501 can be communicatively coupled to a surgical instrument such as a microscope that can include the detector (e.g. a camera). As shown in FIG. 5, the surgical instrument can be a microscope, e.g. a surgical microscope. The surgical instrument may be another type of imaging device such as an ultrasound device, optical coherence tomography device, or camera.

The apparatus 501 can include a memory storage device 520 and/or be coupled to external memory (e.g. one or more memory devices). Images/image data can be accessed in local and/or remote memory, for example. The processor(s) 510 (which can have multiple cores and/or multiple processors) can be used for image processing and the methods described herein.

Herein, the first focal plane, second plane, and third plane can be perpendicular to the optical axis of the imaging device. Alternatively/additionally, the planes are parallel to each other. Alternatively/additionally, the planes are offset from each other.

Herein, the feature, e.g. feature 220, can be an anatomical structure, such as of a patient and/or tissue, e.g. in a field of view.

Herein, the image captured from the first focal plane can be captured immediately after an autofocus procedure.

Herein, a focus offset can be executed with a negligible change of magnification, such as less than 10%, 5%, or 2% change in magnification.

The description above is to illustrate examples to aid understanding, and is not intended to be limiting to the invention defined in the appended claims.

LIST OF REFERENCE SIGNS

The reference signs are:
100 imaging device
101 apparatus
102 processor(s)
103 memory
110 lens assembly
120 feature
141 first focal plane
142 second plane
143 third plane
145 focus position
150 aperture
156 depth of field
170 detector
190 method
192 identify feature
194 determine focus
196 determine aperture
198 outputting
200 imaging device
220 feature
241 first focal plane
242 second plane
243 third plane
245 focus position
250 depth of field
251 maximum depth of field
260 offset
261 depth of field
300 eye
322 second feature
341 first focal plane
342 second plane
343 third plane
345 focus position
351 depth of field
400 eye
422 second feature
423 third feature
442 second plane
443 third plane
445 focus position
451 depth of field
500 imaging device
501 apparatus
510 processor(s)
520 memory

What is claimed is:

1. An apparatus for controlling an imaging device, the apparatus comprising at least one processor and at least one memory, wherein the apparatus is configured to:
    identify a first anatomical feature of from an image captured by the imaging device, wherein the first anatomical feature is on a first focal plane; and
    adjust a focus position and/or an aperture setting of the imaging device,
    wherein the focus position and/or the aperture setting of the imaging device are adjusted such that a second focal plane and/or a third focal plane are within a depth of field of the imaging device, wherein the second focal plane and the third focal plane are planes on which second and third anatomical features are detected or expected, respectively.

2. The apparatus of claim 1, wherein the apparatus is further configured to:

determine at least one of the second focal plane and the third focal plane relative to the first focal plane.

3. The apparatus of claim 1, wherein the apparatus is configured to adjust the focus position of the imaging device by determining an offset from the first focal plane to the adjusted focus position.

4. The apparatus of claim 3, wherein the adjusted focus position is between the second and third planes.

5. The apparatus of claim 3, wherein the aperture setting is adjusted to a maximum aperture of the imaging device for which, at the adjusted focus position, each of the second and third planes is in focus.

6. The apparatus of claim 1, wherein the apparatus is configured to output the adjusted focus position and/or the adjusted aperture setting for controlling a focus and an aperture of the imaging device.

7. The apparatus of claim 1, wherein the apparatus is further configured to control an autofocus procedure to focus to the first focal plane.

8. The apparatus of claim 1, wherein the apparatus is further configured to:
    output a fully open aperture setting for capturing the image.

9. The apparatus of claim 1, wherein the anatomical feature is an iris of an eye of a subject or a corneal limbus of an eye.

10. The apparatus of claim 1, wherein at least one of:
    the focus position, the second plane, and the third plane are configured for including an anteriormost outer surface of a cornea and posterior lens capsule in focus; or
    the focus position, the second plane, and the third plane are configured for including an anteriormost inner surface of a cornea and posterior lens capsule in focus; or
    the focus position, the second plane, and the third plane are configured for including a retina in a center of a field of view and the retina in a periphery of the field of view in focus; or
    the focus position, the second plane, and the third plane are configured for including a nearest surface of a cornea and a farthest surface of the cornea in focus (cornea transplant); or
    the focus position, the second plane, and the third plane are configured for including an anteriormost outer surface of the cornea and the limbus in focus (for endothelial keratoplasties); or
    the focus position, the second plane, and the third plane are configured for including an anteriormost outer surface of the cornea and a plane 800 micrometers posterior thereto in focus (for endothelial keratoplasties).

11. The apparatus of claim 1, wherein the apparatus is further configured to identify the second anatomical feature on the second focal plane, or identify the third anatomical feature on the third focal plane.

12. The apparatus of claim 11, wherein
    the second anatomical feature is a cornea and the third anatomical feature is a posterior lens capsule; or
    the second anatomical feature is a retina at a center of a field of view and the third anatomical feature is at a periphery of the field of view.

13. The apparatus of claim 1, wherein the apparatus is further configured to receive input:
    wherein the input includes at least one of:
    an identification of the first anatomical feature, a depth of field, a first distance from the first focal plane to the second focal plane, a second distance from the first focal plane to the third focal plane, or a third distance from the second focal plane to the third focal plane;

wherein the input is received a user or from memory.

14. The apparatus of claim 1, wherein the apparatus is configured to identify the first anatomical feature by a feature recognition algorithm or by a trained machine learning algorithm.

15. The apparatus of claim 1, wherein the apparatus is configured to determine at least one of the first anatomical feature, the second focal plane, or the third focal plane based on a surgical workflow.

16. The apparatus of claim 1, further comprising:

a detector for capturing images;

an adjustable lens assembly for focusing, and an adjustable aperture, wherein the apparatus is to receive input a second imaging device.

17. The apparatus of claim 1, wherein the apparatus is configured to determine the second plane based on the second anatomical feature on the second focal plane and the third plane based on the third anatomical feature on the third focal plane.

18. A method of controlling an imaging device, comprising:

identifying a first anatomical feature of from an image captured by the imaging device, wherein the first anatomical feature is on a first focal plane;

adjusting a focus position and/or an aperture setting of the imaging device, wherein the focus position and/or the aperture setting of the imaging device are adjusted such that a second focal plane and/or a third focal plane are within a depth of field of the imaging device, wherein the second focal plane and the third focal plane are planes on which second and third anatomical features are detected or expected, respectively.

19. The method of claim 18, wherein at least one of the second focal plane or the third focal plane are determined relative to the first focal plane.

20. A non-transitory, computer-readable medium comprising a program code that, when the program code is executed on a processor, a computer, or a programmable hardware component, causes the processor, computer, or programmable hardware component to perform the method of claim 18.

* * * * *